(12) United States Patent
Naya

(10) Patent No.: US 7,898,659 B2
(45) Date of Patent: Mar. 1, 2011

(54) SURFACE PLASMON SENSOR, SENSING APPARATUS AND SENSING METHOD

(75) Inventor: Masayuki Naya, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 427 days.

(21) Appl. No.: 11/953,303

(22) Filed: Dec. 10, 2007

(65) Prior Publication Data
US 2008/0137063 A1 Jun. 12, 2008

(30) Foreign Application Priority Data

Dec. 11, 2006 (JP) ................................ 2006-332984
Sep. 26, 2007 (JP) ................................ 2007-248990

(51) Int. Cl.
*G01N 21/64* (2006.01)

(52) U.S. Cl. ...................... 356/318; 356/417; 250/458.1

(58) Field of Classification Search .................. 356/317, 356/318, 417
See application file for complete search history.

(56) References Cited

U.S. PATENT DOCUMENTS

| | | | |
|---|---|---|---|
| 6,476,409 B2 | 11/2002 | Iwasaki et al. | |
| 6,610,463 B1 | 8/2003 | Ohkura et al. | |
| 6,784,007 B2 | 8/2004 | Iwasaki et al. | |
| 6,924,023 B2 | 8/2005 | Ohkura et al. | |
| 2005/0105085 A1 | 5/2005 | Naya | |
| 2006/0034729 A1 | 2/2006 | Poponin | |
| 2006/0181701 A1 | 8/2006 | Tomaru | |
| 2009/0032735 A1 * | 2/2009 | Misawa et al. | 250/459.1 |

FOREIGN PATENT DOCUMENTS

| | | |
|---|---|---|
| EP | 1 541 994 A1 | 12/2004 |
| JP | 2001-021565 A | 1/2001 |
| WO | 2006/098446 A1 | 9/2006 |
| WO | 2006/118337 A1 | 11/2006 |

OTHER PUBLICATIONS

Denk et al., "Two-Photon Laser Scanning Fluorescence Microscopy," Science, vol. 248, No. 4951, Apr. 6, 1990, pp. 73-76, XP000381741.

* cited by examiner

*Primary Examiner* — F. L Evans
(74) *Attorney, Agent, or Firm* — Sughrue Mion, PLLC

(57) ABSTRACT

A sensor has a sensing surface, to which a specific substance R to be detected can bind. Further, the sensor has a metal portion, at least a portion of which is exposed at the sensing surface, and in which localized plasmons can be excited. The sensor is used in sensing, in which the substance R to be detected is marked with a fluorescent marker Lu that selectively binds to the substance R to be detected and one of two-photon excitation fluorescence and multi-photon excitation fluorescence of the fluorescent marker Lu is detected. Further, the sensing surface is illuminated with measurement light L1 having a wavelength that can excite localized plasmons in the metal portion and that is an absorption wavelength of the fluorescent marker Lu, at which the fluorescent marker Lu emits one of the two-photon excitation fluorescence and the multi-photon excitation fluorescence.

13 Claims, 5 Drawing Sheets

SURFACE PLASMON SENSOR, SENSING APPARATUS AND SENSING METHOD

BACKGROUND OF THE INVENTION

1. Field of the Invention

The present invention relates to a sensor that is used in sensing, in which a substance to be detected is marked with a fluorescent marker that selectively binds to the substance to be detected and one of two-photon excitation fluorescence and multi-photon excitation fluorescence of the fluorescent marker is detected. The present invention also relates to a sensing apparatus and a sensing method using the sensor.

2. Description of the Related Art

In recent years, fluorescence measurement methods have been proposed in fluorescent analysis that is performed in immunity measurement and the like in the field of biochemistry. In the fluorescence measurement methods, a sensor having a sensing surface, to which a specific substance to be detected can bind, is used. In the methods, a fluorescent marker that has bound to the substance to be detected is excited by evanescent waves or surface plasmons and the substance to be detected is sensed.

In such methods, fluorescence is emitted only when the substance to be detected has bound to the sensing surface. Therefore, real-time measurement is possible. Further, since excitation light does not reach a detector, background light of fluorescence, the fluorescence that should be detected, is small. Therefore, it is possible to perform measurement at a relatively high S/N ratio.

However, in the fluorescence measurement method, substances, such as water, blood serum protein and an enzyme, which coexist with the substance to be detected in a sample, may absorb excitation light. Further, some substance may emit unwanted fluorescence. Further, when surface plasmons are used to excite the fluorescent marker, the substance to be detected needs to be bound to a sensor that is formed by a prism, the surface of which is coated with a thin metal film that generates surface plasmons. If such a sensor is used, the prism absorbs excitation light and emits unwanted fluorescence in some cases. Such absorption of excitation light and emission of fluorescence by coexisting substances or the like, which are not an object of detection, lower the accuracy of detection of fluorescence that should be originally detected.

As a method for performing fluorescence measurement at a higher S/N ratio by suppressing absorption of excitation light and emission of fluorescence by coexisting substances or the like, a two-photon excitation fluorescence measurement method has been proposed. In the two-photon excitation fluorescence measurement method, a fluorescent marker that can be excited by two-photon excitation is used. Two-photon excitation fluorescence is generated by using excitation light that has twice the wavelength of excitation light that is used to generate ordinary fluorescence. Therefore, in the two-photon excitation fluorescence measurement method, it is possible to use excitation light that has a wavelength different from the absorption wavelength of a coexisting substance or the like. Hence, it is possible to perform low-noise fluorescent measurement. Further, since excitation light that has a wavelength in a near-infrared band is used, even if the substance to be detected is living-body tissue, there is no risk that the substance to be detected is damaged by measurement.

However, the cross-sectional area of absorption by two-photon excitation is smaller than that of absorption by single-photon excitation by several tens of digits. Therefore, ordinarily, a very expensive pulse laser that has a high peak value is used to obtain sufficient fluorescence. As a method for obtaining sufficient fluorescence without using such a pulse laser, a method for exciting two-photon excitation fluorescence by surface plasmons has been disclosed (Japanese Unexamined Patent Publication No. 2001-021565).

In Japanese Unexamined Patent Publication No. 2001-021565, features that the probability of transition is increased by at least two digits by exciting two-photon excitation fluorescence by an electric field generated by surface plasmons and the fluorescence efficiency is remarkably improved are described. However, when the surface plasmons are utilized, a sensor formed by a prism that is coated with a thin metal film that generates surface plasmons is required. Further, a complicated optical system is required to emit measurement light and to detect detection light. Therefore, the sensing apparatus tends to be expensive and complicated. Further, even if the probability of transition is increased by approximately two digits, when the size of the cross-sectional area of absorption is taken into consideration, it is not recognized that sufficient fluorescence efficiency is obtained. Therefore, there is still a problem that the fluorescence efficiency has to be improved.

SUMMARY OF THE INVENTION

In view of the foregoing circumstances, it is an object of the present invention to provide a sensor, in which the fluorescence efficiency of fluorescence emitted from a fluorescent marker is high, and which can detect the fluorescence emitted from the fluorescent marker at a high S/N ratio, and that has simple structure and does not require a complicated optical system to emit measurement light and to detect detection light. Further, it is another object of the present invention to provide a sensing apparatus and method using the sensor.

A sensor of the present invention is a sensor used in sensing, the sensor comprising:

a sensing surface, to which a specific substance to be detected can bind, wherein sensing is performed by marking the substance to be detected with a fluorescent marker that selectively binds to the substance to be detected and by detecting one of two-photon excitation fluorescence and multi-photon excitation fluorescence of the fluorescent marker, the sensor further comprising:

a metal portion, at least a portion of which is exposed at the sensing surface, and in which localized plasmons can be excited, wherein the sensing surface is illuminated with measurement light having a wavelength that can excite localized plasmons in the metal portion and that is an absorption wavelength of the fluorescent marker, at which the fluorescent marker emits one of the two-photon excitation fluorescence and the multi-photon excitation fluorescence.

In the specification of the present application, the "two-photon excitation fluorescence" is fluorescence generated by using excitation light that has twice the wavelength of excitation light that is used to generate ordinary fluorescence. Further, the "multi-photon excitation fluorescence" is fluorescence generated by using excitation light that has a wavelength integer times longer than the wavelength of excitation light that is used to generate ordinary fluorescence and the integer is greater than or equal to 3.

In the sensor of the present invention, it is desirable that the metal portion has uneven structure and that the size of the uneven structure is less than the wavelength of the measurement light. Further, it is desirable that surface modification that selectively binds to the substance to be detected is provided on the surface of the metal portion.

In the specification of the present application, the expression "uneven structure, the size of which is less than the wavelength of the measurement light" means that an average size of projection portions and recess portions of the uneven structure (here, the term "size" refers to the greatest width) and an average pitch are less than the wavelength of measurement light. It is not necessary that metal is present in the recess portions.

Further, in a sensor according to a preferred embodiment of the present invention, a substrate of the metal portion is made of a dielectric that has a plurality of minute pores formed therein. Further, the plurality of minute pores have openings at least at the sensing-surface-side surface of the dielectric. The metal portion is formed by a plurality of metal elements, each including a filled portion formed by filling a minute pore in the dielectric and a projection portion formed on the filled portion in such a manner that the projection portion projects from the surface of the dielectric. Further, the diameter of the projection portion is greater than that of the filled portion.

Further, the dielectric may be formed by a metal oxide body that is obtained by anodizing at least a part of a metal body to be anodized and the plurality of minute pores may be formed in the metal oxide body in the anodization process.

Further, in a sensor according to another preferred embodiment of the present invention, the metal portion may be a metal layer that has a rough surface. Alternatively, a substrate of the metal portion may be a dielectric and the metal portion may be a metal particle layer formed by a plurality of metal particles fixed onto the surface of the dielectric. Further, in a sensor according to another preferred embodiment of the present invention, a substrate of the metal portion may be a dielectric and the metal portion may be a metal pattern layer in pattern form that is formed on the surface of the dielectric.

Further, in the sensor of the present invention, it is desirable that the localized plasmon resonance wavelength of the metal portion is substantially the same as the absorption wavelength of the fluorescent marker, at which the fluorescent marker emits one of the two-photon excitation fluorescence and the multi-photon excitation fluorescence. Further, it is desirable that light that has the aforementioned wavelength is used as the measurement light.

Further, in the sensor of the present invention, a transparent insulation layer may be formed on the surface of the metal portion. Specifically, the "transparent insulation layer" is a layer formed by an inorganic material, such as $SiO_2$, or by an organic material, such as a polymer. The transparent insulation layer should substantially transmit light illuminating the surface of the sensor.

Further, surface modification that selectively binds to the substance to be detected may be provided on the surface of the metal portion. The surface modification may be provided directly on the surface of the metal portion or through the transparent insulation layer.

Further, in the sensor of the present invention, the sensing surface may have a single sensing area. Alternatively, the sensing surface may have been divided into a plurality of sensing areas, in each of which sensing is performed independently. If the sensing surface has been divided into the plurality of sensing areas, a different kind of surface modification that is appropriate for a substance to be detected may be provided for each sensing area. If surface modification is provided in such a manner, it is possible to sense different kinds of substances to be detected.

Further, a sensor with a sample cell according to the present invention is a sensor with a sample cell, in which a sensor of the present invention is attached to the sample cell. In the sensor with the sample cell, at least a portion of the sample cell, the portion through which the measurement light and light emitted from the sensing surface pass, transmits light, and the light emitted from the sensing surface includes one of the two-photon excitation fluorescence and the multi-photon excitation fluorescence of the fluorescent marker. In the sensor with the sample cell, the sensor is attached to the sample cell in such a manner that the metal portion of the sensor contacts with a sample in the sample cell.

A sensing apparatus of the present invention is a sensing apparatus comprising:

a sensor of the present invention;

a light illumination means for illuminating the sensor with measurement light; and a detection means for detecting one of two-photon excitation fluorescence and multi-photon excitation fluorescence of a fluorescent marker, the one of which is included in light emitted from the sensor.

It is desirable that the sensing apparatus of the present invention further includes a wavelength selection means for removing light that has the same length as that of the measurement light and that the wavelength selection means is provided in a light path between the sensor and the detection means.

In a sensing apparatus of the present invention, presence of the substance to be detected and/or the amount of the substance to be detected can be analyzed.

A sensing method of the present invention is a sensing method, comprising the steps of:

marking a substance to be detected with a fluorescent marker that selectively binds to the substance to be detected; and detecting one of two-photon excitation fluorescence and multi-photon excitation fluorescence of the fluorescent marker, wherein the one of two-photon excitation fluorescence and multi-photon excitation fluorescence is detected by generating the one of two-photon excitation fluorescence and multi-photon excitation fluorescence by exciting the fluorescent marker by a localized plasmon electric field.

A sensor according to the present invention has a sensing surface, to which a specific substance to be detected can bind. Further, the sensor includes a metal portion and at least a portion of the metal portion is exposed at the sensing surface. In the metal portion, localized plasmons can be excited.

Further, in the sensor of the present invention, sensing is performed by marking a substance to be detected with a fluorescent marker that selectively binds to the substance to be detected and by detecting one of two-photon excitation fluorescence and multi-photon excitation fluorescence of the fluorescent marker.

In the sensor that is structured as described above, when measurement light that has a wavelength that can excite localized plasmons in the metal portion on the sensing surface enters the metal portion, localized plasmons are excited in the metal portion. Therefore, the power of the measurement light is increased in the vicinity of the metal portion by an electric field enhancement effect of the localized plasmons. Hence, it is possible to increase the probability of transition of the fluorescent marker that has bound to the metal portion and to effectively improve the fluorescence efficiency.

Further, in the sensor of the present invention, one of the two-photon excitation fluorescence and the multi-photon excitation fluorescence of a fluorescent marker is utilized. Therefore, measurement light that has at least twice the wavelength of excitation light for single-photon excitation is used. Hence, it is possible to suppress absorption of the measurement light and emission of fluorescence by a coexisting material and it becomes possible to detect fluorescence at a higher S/N ratio.

Further, in the sensor of the present invention, it is sufficient if the sensor includes a metal portion, at least a portion of which is exposed at the sensing surface, and in which localized plasmons can be excited. Therefore, the structure of the sensor itself is simple and a complicated optical system is not required in the measurement system. Hence, the structure of the sensing apparatus can be simplified.

Further, if a transparent insulation layer is formed on the surface of the metal portion, surface modification that selectively binds to a substance to be detected is provided on the surface of the metal portion through the transparent insulation layer. Therefore, direct movement of charges from the fluorescent marker that has bound to the surface modification to the surface of the metal portion is prevented. Hence, there is no risk that fluorescence emitted from the fluorescent marker is weakened by the direct movement of the charges.

DESCRIPTION OF THE PREFERRED EMBODIMENTS

Sensor

Figure 1A:
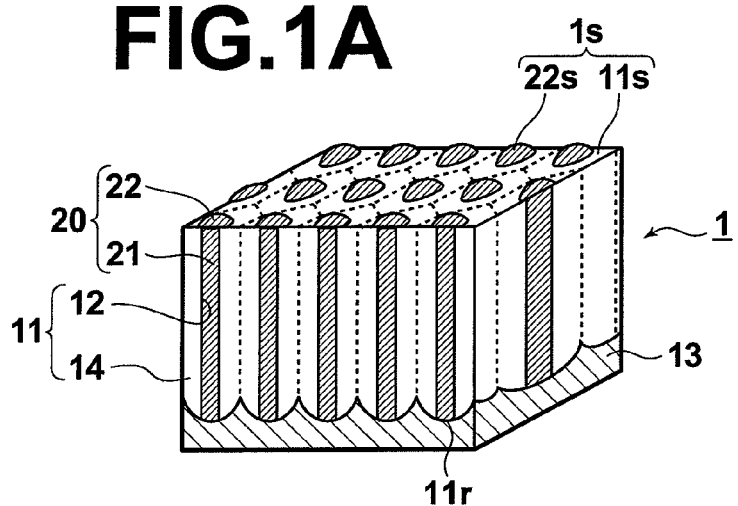
FIG. 1A is a perspective view showing the whole structure of a sensor according to an embodiment of the present invention.
Figure 1B:
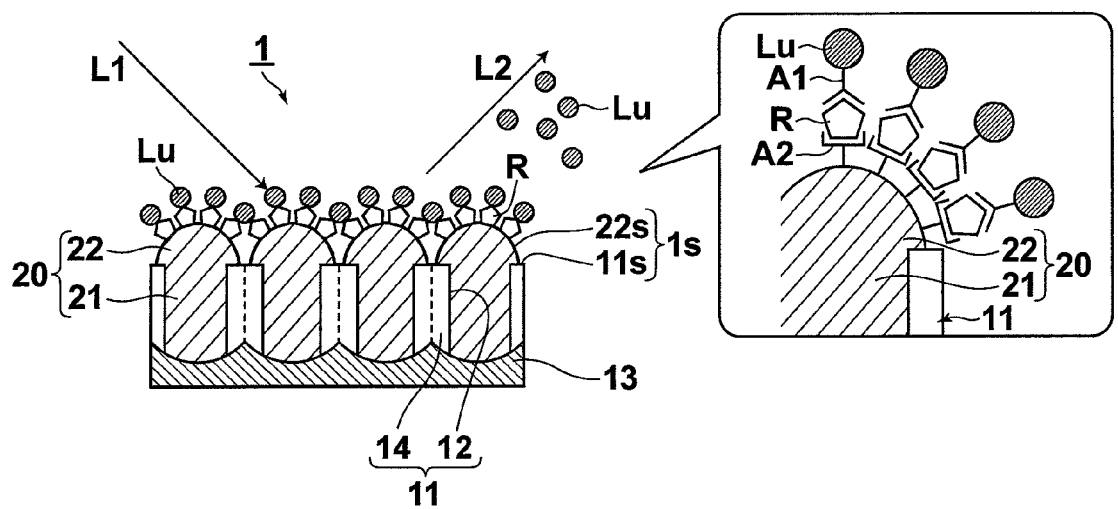
FIG. 1B is a cross-sectional view of the sensor according to an embodiment of the present invention in the thickness direction of the sensor during sensing.
Figure 2A:
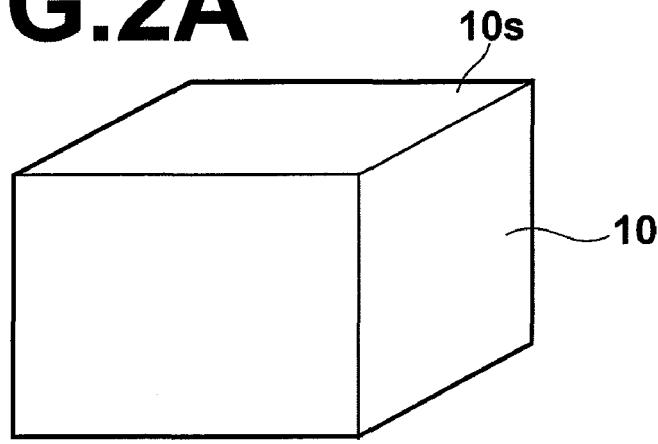
FIG. 2A is a diagram illustrating a process of producing the sensor illustrated in FIGS. 1A and 1B.
Figure 2B:
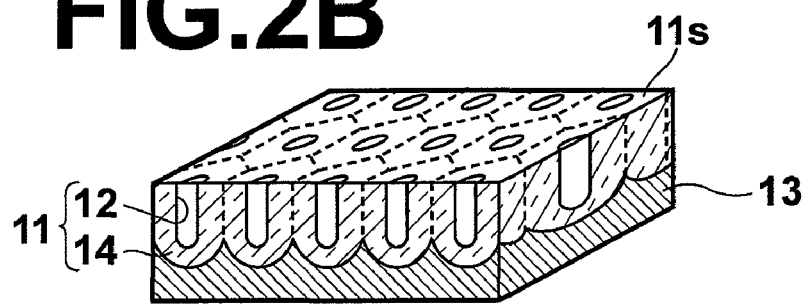
FIG. 2B is a diagram illustrating a process of producing the sensor illustrated in FIGS. 1A and 1B.
Figure 2C:
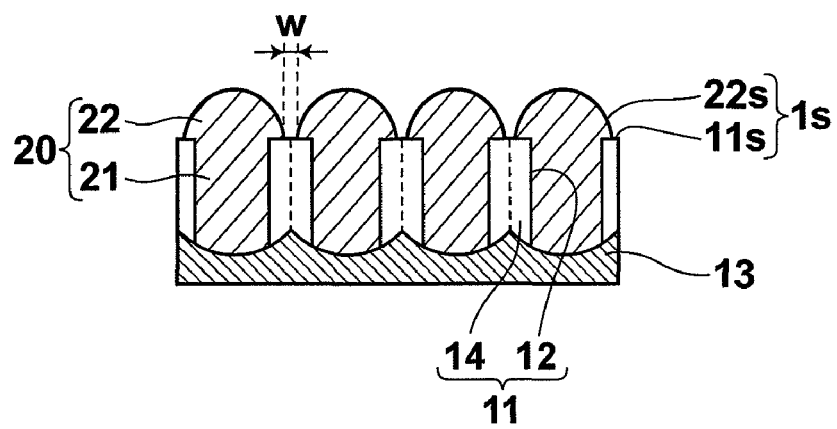
FIG. 2C is a diagram illustrating a process of producing the sensor illustrated in FIGS. 1A and 1B.

The structure of a sensor according to an embodiment of the present invention will be described with reference to the attached drawings. FIG. 1A is a perspective view showing the whole structure of the sensor. FIG. 1B is a cross-sectional view of the sensor in the thickness direction of the sensor during sensing. Further, FIG. 1B includes a schematic diagram illustrating a binding state at a sensing surface during sensing. FIGS. 2A through 2C are diagrams illustrating the process of producing the sensor according to the present embodiment.

A sensor 1 according to the present embodiment is used in sensing, in which a substance R to be detected is marked with a fluorescent marker Lu that selectively binds to the substance R to be detected and one of two-photon excitation fluorescence and multi-photon excitation fluorescence of the fluorescent marker Lu is detected. The sensor 1 includes a sensing surface 1s, to which only the substance R to be detected can bind.

In the present embodiment, the sensor 1 includes a metal portion 20, at least a portion of which is exposed at a sensing surface 1s, and in which localized plasmons can be excited. In the sensor 1, the sensing surface 1s is illuminated with measurement light L1. The measurement light L1 has a wavelength that can excite localized plasmons in the metal portion 20 and an absorption wavelength of the fluorescent marker, at which the fluorescent marker emits one of the two-photon excitation fluorescence and the multi-photon excitation fluorescence.

The measurement light L1 is single-wavelength light that is emitted from a light source, such as a laser.

Further, it is desirable that the metal portion 20 forming a part of the sensing surface 1s has uneven structure, the size of which is less than the wavelength of the measurement light L1, to achieve a high localized plasmon effect.

As illustrated in FIG. 1A, the sensor 1 includes a dielectric substrate 11 on an electrically conductive member 13. In the dielectric substrate 11, a multiplicity of minute pores 12 are substantially regularly distributed and the minute pores 12 have openings at the surface of the dielectric substrate 11. Further, the sensor 1 includes a metal portion 20 having a filled portion 21 and a projection portion 22. The filled portion 21 is a portion formed by filling the inside of the minute pore 12. The projection portion 22 is formed on the minute pore 12 in such a manner to project from a substrate surface 11s. The diameter of the projection portion 22 is larger than that of the filled portion 21 and the diameter of the projection portion 22 is a size that can excite localized plasmons.

In the sensor 1, the projection-portion-22-side surface of the metal portion 20 is the sensing surface 1s. Specifically, in the present embodiment, the sensing surface 1s is formed by the substrate surface 11s and a surface 22s of the projection portion 22.

In the sensor 1, the minute pores 12 are through-holes that penetrate through the dielectric substrate 11 in the thickness direction of the dielectric substrate 11 from the projection-portion-22-side surface of the metal portion 20. The through-holes are substantially straight and reach a substrate back-surface 11r.

As illustrated in FIGS. 2A through 2C, the dielectric substrate 11 is an alumina ($Al_2O_3$) layer (metal oxide layer). The alumina layer is obtained by anodizing a part of a metal body 10 to be anodized that contains aluminum (Al) as a main component. The metal body 10 to be anodized may contain a very small amount of impurities. The electrically conductive member 13 is formed by a portion of the metal body 10 to be anodized, the portion that has not been anodized.

The shape of the metal body 10 to be anodized is not particularly limited. The shape may be a plate shape or the like. Further, the metal body 10 to be anodized may have a member supporting the metal body 10 to be anodized. For example, the metal body 10 to be anodized may be layers formed on a support member or the like.

Anodization may be performed by using the metal body 10 to be anodized as an anode (positive electrode) and carbon, aluminum or the like as a cathode (negative electrode or opposite electrode), for example. These electrodes are immersed in electrolyte and voltage is applied between the anode and the cathode to perform anodization. The kind of the electrolyte is not limited. Optionally, an acid electrolyte containing one or two kinds of acids selected from sulfuric acid, phosphoric acid, chromic acid, oxalic acid, sulfamic acid, benzenesulfonic acid, amidosulfonic acid and the like may be used.

When the metal body 10 to be anodized illustrated in FIG. 2A is anodized, oxidation starts at a surface 10s (the upper surface in FIG. 2B) of the metal body 10 to be anodized and proceeds in a direction substantially vertical to the surface 10s. Consequently, an alumina layer 11 is formed, as illustrated in FIG. 2B.

The alumina layer 11 that is formed by anodization has structure, in which very thin column-shaped bodies 14 are formed next to each other. Each of the very thin column-shaped bodies 14 has a substantially equilateral hexagonal shape when they are viewed from a plan-view direction. Further, a minute pore 12 is formed substantially at the center of each of the very thin column-shaped bodies 14. The minute pore 12 is formed in the thickness direction of the alumina layer 11 from the surface 10s. Further, the bottom of each of the minute pores 12 and the bottom of each of the very thin column-shaped bodies 14 have rounded shapes as illustrated in FIGS. 2B and 2C. The structure of an alumina layer formed by anodization is described in H. Masuda, "Preparation of Mesoporous Alumina by Anodization and Application Thereof as Functional Material", Material Technique Vol. 15, No. 10, 1997, p. 34 and the like.

An example of a desirable anodization condition for forming an alumina layer 11 that has regularly-distributed structure is as follows. When oxalic acid is used as electrolyte, the concentration of the electrolyte should be 0.5M, the liquid temperature should be 15° C., and the application voltage should be 40V, for example. An alumina layer 11 that has an arbitrary thickness can be formed by changing electrolysis time.

Ordinarily, a pitch of the minute pores 12 formed next to each other can be controlled in a range of 10 to 500 nm. Further, the diameters of the minute pores 12 can be controlled in a range of 5 to 400 nm. Further, in U.S. Pat. Nos. 6,476,409, 6,784,007, 6,610,463, and 6,924,023, methods for more precisely controlling the formation positions of the minute pores and the diameters of the minute pores are disclosed. If these methods are used, it is possible to substantially regularly form minute pores that have arbitrary diameters and depths within the aforementioned ranges.

Further, the metal portion 20 including the filled portion 21 and the projection portion 22 is formed by performing electroplating or the like on the minute pore 12 of the dielectric substrate 11.

When electroplating is performed, the electrically conductive member 13 functions as an electrode and metal precipitates. Since the electric field at the bottom portion of the minute pore 12 is strong, metal precipitates in the bottom portion of the minute pore 12 prior to the other portion of the minute pore 12. If electroplating is continuously performed, the minute pore 12 is filled with metal and the filled portion 21 of the metal portion 20 is formed. Further, if electroplating is continued after formation of the filled portion 21, the metal that has filled the minute pore 12 overflows therefrom. However, since the electric field in the vicinity of each of the minute pores 12 is strong, the metal continuously precipitates in the vicinity of each of the pores 12. Accordingly, a projection portion 22 is formed on the filled portion 21. The projection portion 22 projects from the substrate surface 11s and has a diameter that is greater than that of the filled portion 21.

When the metal portion 20 grows (becomes bigger) by electroplating, a thin layer between the bottom of the minute pore 12 and the electrically conductive member 13 is penetrated (destroyed) under some conditions. Then, the filled portion 21 of the metal portion 20 reaches the substrate back-surface 11r. The electrically conductive member 13 is a member formed by a portion of the metal body 10 to be anodized, the portion that has not been anodized. Accordingly, the structure of the present embodiment is obtained (FIG. 2C).

In the present embodiment, the projection portion 22 of the metal portion 20 has a particle shape. Further, if the sensor 1 is observed from the surface side of the sensor, a metal particle layer is formed on the substrate surface 11s. In such structure, the projection portion 22 is a convex portion (projection portion) of the metal portion 20. Therefore, it is desirable that the projection portions 22 are designed in such a manner that an average diameter of the projection portions 22 and an average pitch are less than the wavelength of measurement light L1. In the metal portion 20, it is sufficient if the size of the projection portion 22 is a size that can excite localized plasmons. However, if consideration is given to the wavelength of measurement light that is used in sensing, it is desirable that the diameter of the projection portion 22 is greater than or equal to 10 nm and less than or equal to 300 nm.

It is desirable that the projection portions 22 that are next to each other are apart from each other. Further, it is desirable that an average distance w between adjacent projection portions is in a range of a few nm to 10 nm. If the average distance w is in this range, an electric field enhancement effect by localized plasmons can be effectively obtained.

A localized plasmon phenomenon is a phenomenon, in which a very strong electric field is generated in the vicinity of a projection portion. The very strong electric field is generated because free electrons in the projection portion resonate with an electric field of light and vibrate. Therefore, the metal portion 20 may be made of an arbitrary metal having free electrons. In the sensor 1, the sensing surface 1s is illuminated with measurement light L1. The measurement light L1 has a wavelength that can excite localized plasmons in the metal portion 20 on the sensing surface 1s. Specifically, the wavelength is a wavelength that can excite localized plasmons at the projection portion 22. Further, the wavelength of the measurement light L1 is an absorption wavelength of the fluorescent marker Lu, at which the fluorescent marker Lu emits one of the two-photon excitation fluorescence and the multi-photon excitation fluorescence. Therefore, it is desirable that the combination of the fluorescent marker Lu and the metal portion 20 is determined so that the fluorescent marker Lu emits fluorescent at high efficiency. Further, as the material of the metal portion 20, metal that generates localized plasmons at a wavelength that is substantially the same as an absorption wavelength of the fluorescent marker Lu, at which the fluorescent marker Lu emits one of the two-photon excitation fluorescence and the multi-photon excitation fluorescence, is desirable. Further, if the wavelength of excitation light for the fluorescent marker Lu, which will be described later, is taken into consideration, it is desirable that Au, Ag, Cu, Pt, Ni, Ti or the like is used as the material for the metal portion 20.

Further, if noise generated by absorption of excitation light by a coexisting substance or the like in a sample and by emission of fluorescence by the coexisting substance or the like is taken into consideration, a fluorescent marker that has an absorption wavelength in a near-infrared band or a longer wavelength band and that is capable of two-photon excitation or multi-photon excitation is desirable. Examples of such a fluorescent marker are R6G, Cye5 and the like.

As illustrated in FIG. 1B, surface modification A2 has been provided on a surface 22s of the projection portion 22 on the sensing surface 1s. The surface modification A2 can selectively binds to a substance R to be detected. In the sensor 1 according to the present embodiment, the substance R to be detected is marked with the fluorescent marker Lu that has bound to the substance R to be detected in advance, and sensing is performed. Further, surface modification A1 has been provided on the fluorescent marker Lu. The surface modification A1 selectively binds to the substance R to be detected.

The binding reaction between the substance R to be detected and the fluorescent marker Lu and the reaction between the projection portion 22 and the substance R to be detected are not particularly limited. The reactions may be a specific-binding reaction, such as an antigen-antibody reaction, and the like.

For example, if the substance R to be detected is an antigen, surface modification (surface modification A1) should be provided on the fluorescent marker Lu by using a first antibody that specifically binds to the substance R to be detected. Further, surface modification (surface modification A2) should be provided on the projection portion 22 by using a second antibody that specifically binds to the substance R to be detected. As illustrated in FIG. 1B, the first antibody, as surface modification, is provided for the fluorescent marker Lu. Further, the second antibody, as surface modification, is provided for the projection portion 22. The first antibody and the second antibody that bind to different portions of the substance R to be detected, which is an antigen, are used. Specifically, surface modification is provided for the projection portion 22 and the fluorescent marker Lu in such a manner that the surface modification A2 on the projection portion 22, the substance R to be detected and the surface modification A1 on the fluorescent marker Lu bind to each other, as illustrated in FIG. 1B.

Next, process of sensing using the sensor 1 according to the present embodiment will be described.

First, a sample is poured (or caused to flow) on a sensing surface 1s. If the sample includes a substance R to be detected, the substance R to be detected binds to the surface modification A2 on the projection portion 22. Then, liquid containing fluorescent marker Lu, for which surface modification A1 has been provided in advance, is poured on the sensing surface 1s. If the substance R to be detected has bound to the projection portion 22, the substance R to be detected binds to the fluorescent marker Lu.

Instead of sequentially pouring the sample and the liquid containing the fluorescent marker Lu, the fluorescent marker Lu may be added to the sample in advance. If the sample contains the substance R to be detected, the substance R to be detected and the fluorescent marker Lu bind to each other before the sample is poured on the sensing surface 1s. Then, sensing may be performed by pouring only the sample on the sensing surface 1s.

When measurement light L1 enters the sensing surface 1s, at which the fluorescent marker Lu has bound to the projection portion 22, the fluorescent marker Lu emits one of two-photon excitation fluorescence and multi-photon excitation fluorescence at a certain probability of transition. Then, the substance R to be detected can be sensed by detecting the fluorescence. In the sensor 1, the fluorescent marker Lu is excited by the measurement light L1 and fluorescence is emitted. At the same time, in the metal forming the projection portion 22, localized plasmons are excited. When localized plasmons are excited in metal, an electric field in the vicinity of the surface of the metal becomes strong. Therefore, the power of the measurement light L1 is increased in the vicinity of the projection portion 22 and the probability of transition of the fluorescent marker Lu is increased. If the probability of transition is increased, the intensity of fluorescence increases. Hence, sensing can be performed at higher sensitivity.

For example, the probability of transition by ordinary single-photon absorption is proportional to the power of excitation light. In two-photon absorption, the probability of transition is proportional to the square of the power of the excitation light. Hence, the probability of transition is increased by the square of an electric field enhancement effect of localized plasmons.

It is said that the electric field enhancement effect by localized plasmons is greater than or equal to 100 times when the wavelength is a localized plasmon resonance wavelength. Therefore, it is desirable that light that has a wavelength at which localized plasmon resonance is induced at the projection portion 22 is used as the measurement light L1. In such a case, it is possible to improve the probability of transition by at least four digits.

As described above, sensing can be performed using the sensor 1 according to the present embodiment.

The sensor 1 according to the present embodiment includes the sensing surface 1s, to which only a specific substance R to be detected can bind. Further, the sensor 1 includes a metal portion 20, at least a portion of which is exposed at the sensing surface 1s, and in which localized plasmons can be excited. In the sensor 1 according to the present embodiment, the substance R to be detected is marked with the fluorescent marker Lu that selectively binds to the substance R to be detected. Then, sensing is performed by detecting one of two-photon excitation fluorescence and the multi-photon excitation fluorescence of the fluorescent marker Lu.

Since the sensor 1 is structured as described above, when measurement light L1 having a wavelength that can excite localized plasmons in the metal portion 20 enters the metal portion 20 on the sensing surface 1s, localized plasmons are excited at the metal portion 20. Then, the power of the measurement light L1 in the vicinity of the metal portion 20 is increased by the electric field enhancement effect of the localized plasmons. Therefore, the probability of transition of the fluorescent marker Lu that has bound to the metal portion 20 is increased. Hence, it is possible to effectively improve the fluorescence efficiency.

Further, the sensor 1 according to the present embodiment performs sensing by utilizing two-photon excitation fluorescence or multi-photon excitation fluorescence of the fluorescent marker Lu. Therefore, it is possible to use measurement light having a wavelength that is at least twice the wavelength of measurement light for single-photon excitation. Hence, it is possible to suppress absorption of the measurement light L1 by a coexisting substance and the like and emission of fluorescence by the coexisting substance or the like. Consequently, it is possible to detect fluorescence at a high S/N ratio.

Further, in the sensor 1 according to the present embodiment, it is sufficient if the sensor 1 includes the metal portion 20, at least a portion of which is exposed at the sensing surface 1s, and in which localized plasmons can be excited. Therefore, it is possible to simplify the structure of the sensor itself.

In the sensor 1 according to the present embodiment, the sensing surface 1s may have a single sensing area. Alternatively, the sensing surface 1s may have a plurality of sensing areas formed by dividing the sensing surface 1s. In each of the plurality of sensing areas, sensing may be performed independently. When the sensing surface 1s is divided into the plurality of sensing areas, a different kind of surface modification A2 that is appropriate for a substance R to be detected may be provided for each of the sensing areas. If the surface modification A2 is provided in such a manner, it is possible to sense different kinds of substances R to be detected.

As described above, according to the present embodiment, the fluorescent efficiency of fluorescence emitted from the fluorescent marker Lu is high. Further, it is possible to detect the fluorescence emitted from the fluorescent marker Lu at a high S/N ratio. Further, it is possible to provide the sensor 1, which has simple structure, and which does not require a complicated optical system for emitting measurement light and for detecting detection light.

<Design Modification>

In the method described in the aforementioned embodiment, the alumina layer obtained by anodizing a portion of the metal body 10 to be anodized is used as the dielectric substrate 11. Further, a portion of the metal body 10 to be anodized, the portion that has not been anodized, is used as the electrically conductive member 13. Further, the metal portion 20 is formed by precipitating metal in the minute pore 12 in the dielectric substrate 11. Alternatively, the entire metal body 10 to be anodized may be anodized or after a portion of the metal body 10 to be anodized is anodized, a non-anodized portion and the vicinity of the non-anodized portion may be removed. Then, a dielectric substrate 11 including minute pores 12 forming through-holes can be obtained. Further, an electrically conductive member 13 may be separately deposited on the dielectric substrate 11 by vapor deposition or the like. In this case, the material of the electrically conductive member 13 is not limited. The material of the electrically conductive member 13 may be an electrically conductive material, such as an arbitrary metal and ITO (indium tin oxide).

Further, in the aforementioned embodiment, a case in which the electrically conductive member 13 is provided on the substrate back-surface 11r has been described. However, if a method that does not require an electrode for electroplating or the like is adopted as a method for filling the minute pore 12 with the metal portion 20, it is not necessary that the electrically conductive member 13 is provided. Further, the electrically conductive member 13 may be removed after forming the metal portion 20.

In the aforementioned embodiment, a case in which the minute pore 12 is a through-hole has been described. However, it is not necessary that the minute pore 12 is a through-hole.

In the aforementioned embodiment, only Al is mentioned as an example of the main component of the metal body 10 to be anodized, the metal body 10 being used to produce the dielectric substrate 11. However, an arbitrary metal may be used as the main component as long as the metal can be anodized. For example, Ti, Ta, Hf, Zr, Si, In, Zn and the like may be used instead of Al. The metal body 10 to be anodized may contain two or more kinds of metals that can be anodized.

The flat pattern of a minute pore 12 that is formed by anodization differs according to the kind of the metal to be anodized, which is used for anodization. Even if a different kind of metal is used, a dielectric substrate 11 that has structure in which minute pores 12 are formed next to each other can be formed. Further, the minute pores 12 have substantially the same shapes when they are viewed in a plan-view direction.

So far, cases in which regularly-distributed minute pores 12 are formed by utilizing anodization have been described. However, the method for forming the minute pores 12 is not limited to the anodization. If anodization is utilized, the entire surface can be processed at once and even a large area can be processed. Further, an expensive apparatus is not required. Therefore, the aforementioned embodiment utilizing anodization is desirable. However, the minute pores 12 may be formed by utilizing microfabrication techniques. For example, a plurality of regularly-distributed recesses may be formed on the surface of a substrate made of a resin or the like by utilizing a nanoimprint technique. Alternatively, a plurality of regularly-distributed recesses may be drawn on the surface of a substrate made of metal or the like by utilizing an electronic drawing technique, such as a focused ion beam (FIB) technique and an electronic beam (EB) technique.

Figure 3A:
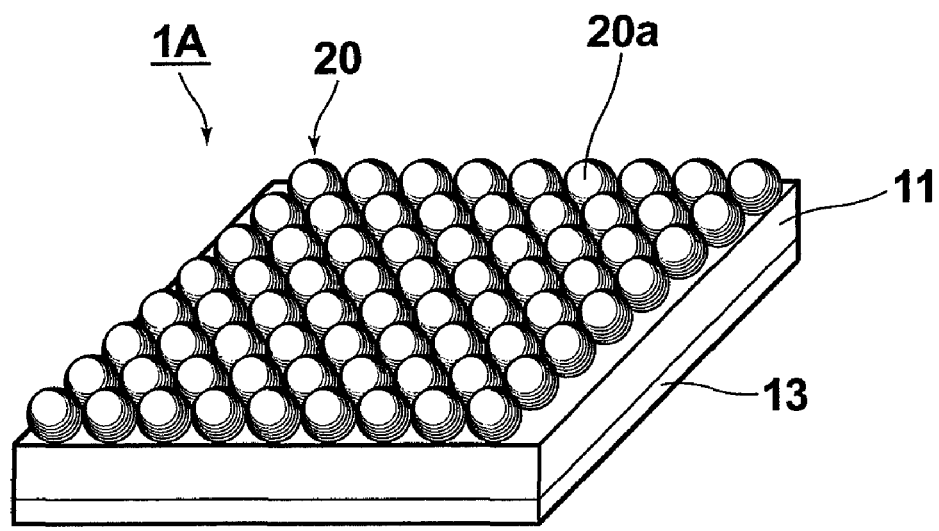
FIG. 3A is a diagram illustrating a design modification example of the sensor illustrated in FIGS. 1A and 1B.
Figure 3B:
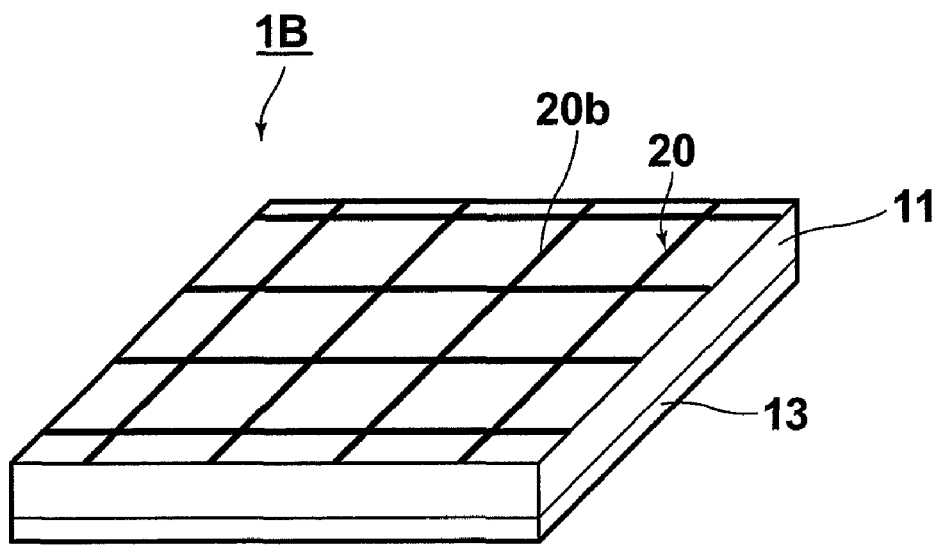
FIG. 3B is a diagram illustrating a design modification example of the sensor illustrated in FIGS. 1A and 1B.

Further, according to other preferred embodiments of the present invention, the sensor 1 may be sensors 1A through 1F, illustrated in FIGS. 3A, 3B, 4A through 4C and 5. With reference to FIGS. 3A, 3B, 4A through 4C and 5, the preferred embodiments of the present invention will be described. FIGS. 3A and 3B are perspective views and FIGS. 4A through 4C and 5 are cross-sectional views.

The sensor 1A illustrated in FIG. 3A is a device in which a plurality of metal particles 20a in array form are fixed onto a flat dielectric body 11. In this example, the metal portion 20 is a metal particle layer formed by the plurality of metal particles 20a. The arrangement pattern of the metal particles 20a may be appropriately designed. It is desirable that the arrangement pattern is a substantially regular pattern. In this structure, each of the metal particles 20a is a projection portion. Further, the metal particle layer is designed in such a manner that an average diameter of the metal particles 20a and a pitch of the metal particles 20a are less than the wavelength of the measurement light L1.

The sensor 1B illustrated in FIG. 3B is a device in which a metal portion 20 formed by a metal pattern layer is formed on a flat dielectric body 11. The metal pattern layer is a layer in which metal thin wires 20b in grid form are formed by pattern formation. The pattern of the metal pattern layer may be appropriately designed. It is desirable that the pattern is a substantially regular pattern. In this structure, the metal pattern layer is designed in such a manner that an average width of the metal thin wires 20b and a pitch of the metal thin wires 20b are less than the wavelength of the measurement light L1.

In the sensor 1, the sensing surface 1s may be formed only by the metal portion 20, in which localized plasmons can be excited.

Figure 4A:
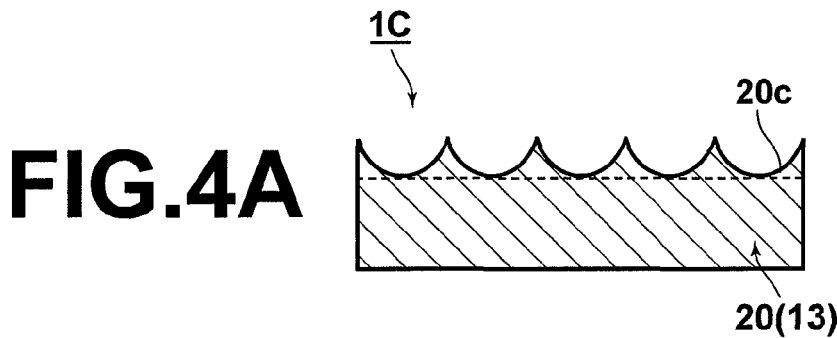
FIG. 4A is a diagram illustrating a design modification example of the sensor illustrated in FIGS. 1A and 1B.

The sensor 1C illustrated in FIG. 4A is a device formed by performing anodization as illustrated in FIGS. 2A and 2B and by removing the alumina layer 11 formed by anodization so that only the non-anodized portion of the metal body to be anodized is left (please refer to U.S. Patent Application Publication No. 20060181701). In this device, the metal portion 20 is formed by an electrically conductive member 13 formed by the non-anodized portion, and the non-anodized portion has a plurality of dimple-shaped recesses 20c.

Figure 4B:
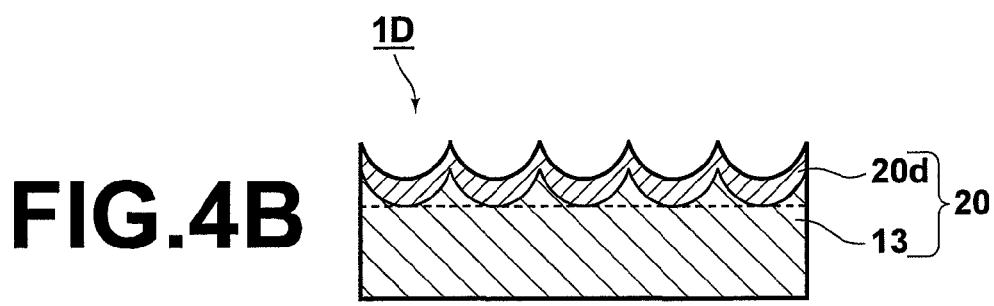
FIG. 4B is a diagram illustrating a design modification example of the sensor illustrated in FIGS. 1A and 1B.

The sensor 1D illustrated in FIG. 4B is a device in which a metal layer 20d has been deposited on the surface of the sensor 1C along the uneven shape of the surface (please refer to U.S. Patent Application Publication No. 20060181701).

Figure 4C:
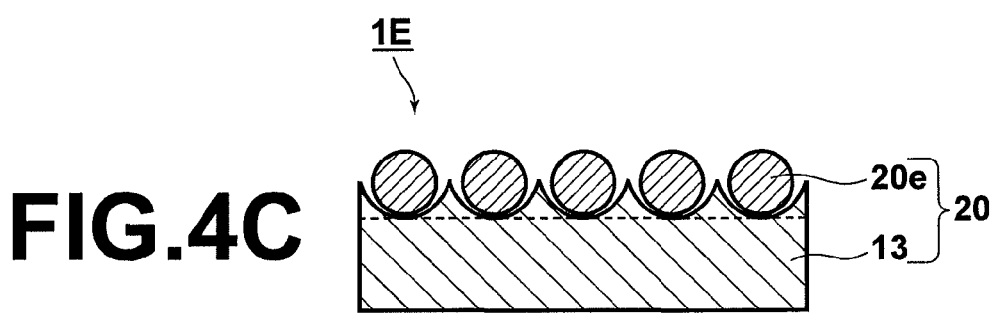
FIG. 4C is a diagram illustrating a design modification example of the sensor illustrated in FIGS. 1A and 1B.

The sensor 1E illustrated in FIG. 4C is a device in which metal particles 20e are formed on the non-anodized portion 13 of the metal body to be anodized. The metal particles 20e are formed by forming the metal layer 20d of the sensor 1D into particle shapes by annealing (please refer to Japanese Patent Application No. 2006-198009 (Japanese Patent Application No. 2006-198009 was not published when the corresponding Japanese patent application of the present application was filed)).

In the sensors 1A through 1E illustrated in FIGS. 3A, 3B and 4A through 4C, a metal portion 20 that has substantially regular uneven structure is obtained. Therefore, a uniform localized plasmon effect is obtained in the entire surface of the device.

The metal portion 20 may be formed by a metal layer that has a rough surface. As a method for forming the rough surface, an electrochemical method utilizing oxidation/reduction or the like may be used.

Figure 5:
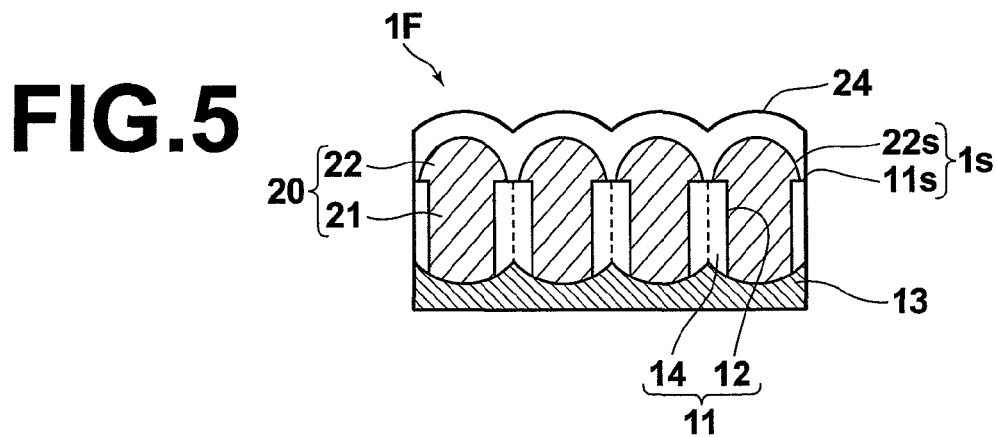
FIG. 5 is a diagram illustrating a modification example of the sensor illustrated in FIGS. 1A and 1B.

The sensor 1F illustrated in FIG. 5 is a device in which a transparent insulation layer 24 is formed on the surface of the sensor 1 illustrated in FIGS. 1A and 1B along the uneven shape of the surface of the sensor 1. In this case, surface modification A2 is provided on the projection portion 22 of the metal portion 20 through the transparent insulation layer 24. The transparent insulation layer 24 is an $SiO_2$ layer that has a thickness of 50 nm or less. The transparent insulation layer 24 substantially transmits measurement light L1 that illuminates the surface of the sensor 1. The main function of the transparent insulation layer 24 is to prevent direct movement of charges from the fluorescent marker Lu to the projection portion 22. The fluorescent marker Lu is bound to surface modification A1 and the surface modification A1 is bound to the substance R to be detected. Further, the substance R to be detected is bound to surface modification A2. Generally, the degree of movement of energy from a substance that is present in the vicinity of a metal to the metal is in inverse proportion to the third power of the distance therebetween if the metal is a flat plane having a semi-infinite thickness. If the metal is a substantially infinitely thin flat plate, the degree of movement of energy from a substance in the vicinity of a metal to the metal is in inverse proportion to the fourth power of the distance therebetween. Further, if the metal is minute particles, the degree of movement of energy from a substance in the vicinity of a metal to the metal is in inverse proportion to the sixth power of the distance therebetween. The degree of movement of energy becomes smaller as described above. In the sensor 1, the thickness of the transparent insulation layer 24 that can prevent direct movement of charges from the fluorescent marker Lu to the projection portion 22 differs according to the material, size, shape and the like of the projection portion 22. The thickness of the transparent insulation layer 24 is in a range of approximately a few nm to tens of nm. It is desirable that the transparent insulation layer 24 has a thickness that is greater than or equal to a thickness that can prevent the direct movement of the charges. Meanwhile, it is known that the electric field enhancement effect by the localized plasmon effect exponentially attenuates as the distance from the metal surface increases. Further, the degree of the electric field enhancement effect is affected by the shape of the metal surface. Therefore, if consideration is given to the diameter of the projection portion 22 and the shape of the projection portion 22 in the present embodiment, it is desirable that the thickness of the transparent insulation layer 24 is less than or equal to 50 nm so that an effective electric field enhancement effect is obtained.

Further, the material of the transparent insulation layer 24 is not limited to $Sio_2$ film. The material of the transparent insulation layer 24 may optionally be a polymer. Specifically, the material of the transparent insulation layer 24 may be a hydrophobic high polymer, an inorganic oxide or the like.

It is desirable that the hydrophobic high polymer contains a monomer, of which the solubility in water is less than or equal to 20 wt % (weight percent), at greater than or equal to 50 wt %. As examples of the monomer that has solubility in water of less than or equal to 20 wt %, there are vinyl esters, acrylic acid esters, methacrylic acid esters, olefines, styrenes, crotonic acid esters, itaconic acid diesters, maleic acid diesters, fumaric acid diesters, allyl compounds, vinyl ethers, vinyl ketones and the like. An arbitrary substance may be selected therefrom. Optionally, styrene, methacrylic acid methyl, methacrylic acid hexafluoropropane, vinyl acetate, acrylonitrile or the like may be used. The hydrophobic high polymer may be a homopolymer, which is formed by one kind of monomer, or a copolymer, which is formed by at least two kinds of monomers.

Further, a high polymer, in which monomers that have solubility in water of 20 wt % or higher are copolymerized with each other, may be used at the same time. As examples of the monomer that has solubility in water of 20 wt % or higher, there are 2-hydroxyethyl methacrylic acid, methacrylic acid, acrylic acid, allyl alcohol and the like. Optionally, as hydrophobic high polymer, polyacrylic acid ester, polymethacrylic ester, polyester, polyethylene or the like may be used. If such substance is used, it becomes possible to easily form a layer. Further, it becomes possible to easily expose a functional group for fixing a physiologically active substance thereto at the surface of the layer. For example, when the layer (coating) is made of polyacrylic acid ester, polymethacrylic acid ester or polyester, it is possible to easily expose carboxyl groups and hydroxyl groups at the surface of the layer by hydrolyzing the surface of the layer with acid or base. Further, when the layer (coating) is made of polystyrene, it is possible to easily expose carboxyl groups at the surface of the layer by performing oxidation processing, such as UV/ozone processing, on the surface of the layer.

As inorganic oxides that can be used as the material of the transparent insulation layer, silica, alumina, titania, zirconia, ferrite or the like, their composites or a dielectric may be selected.

The transparent insulation layer 24 may be formed by using an ordinary method. For example, a method, such as a sol-gel method, a sputter method, a vapor deposition method or a plating method, may be adopted.

"Sensor with Sample Cell"

Figure 6:
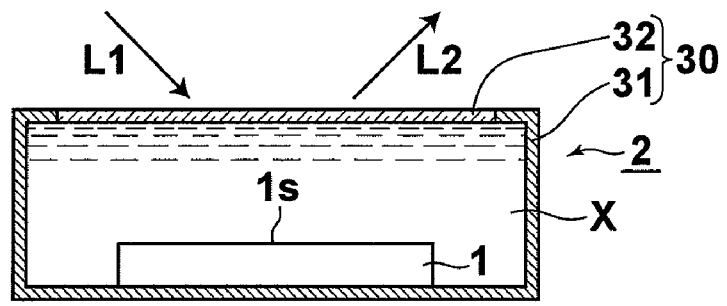
FIG. 6 is a schematic cross-sectional view showing the structure of a sensor with a sample cell according to an embodiment of the present invention.

The structure of a sensor with a sample cell according to an embodiment of the present invention will be described with reference to FIG. 6. FIG. 6 is a cross-sectional diagram corresponding to FIG. 1B.

In a sensor with a sample cell 2 according to the present embodiment, the sensor 1 according to the aforementioned embodiment is fixed to a sample cell 30 so that the metal portion 20 of the sensor 1 contacts with a sample in the sample cell 30 (a structure for fixing is omitted in the diagram).

The sample cell 30 is mainly formed by a cell main body 31 that can be filled with sample X. The cell main body 31 is made of a non-light-transmissive material. Further, a window 32 is fitted onto the cell main body 31. The window 32 is fitted onto a side of the cell main body 31, the side facing the sensing surface 1s of the sensor 1.

The sample X can be injected into the sample cell 30 and discharged from the sample cell 30. The sample cell 30 may be a flow cell, which continuously receives and outputs the sample X.

In the sensor with the sample cell 2, the sensor 1 should be fixed in such a manner that the sensing surface 1s contacts with the sample X filled in the sample cell 30. As illustrated in FIG. 6, the whole sensor may be stored in the sample cell 30. Alternatively, the sensor 1 may be fitted onto a wall of the sample cell 30, the wall facing a wall of the sample cell 30, onto which the window 32 is fitted. Further, the sensor 1 may be completely fixed to the sample cell 30. Alternatively, the sensor 1 may be fixed to the sample cell 30 in a detachable manner.

In the sensor with the sample cell 2, measurement light L1 enters the sample cell 30 through the window 32, which transmits light, and illuminates the sensing surface 1s of the sensor 1. Then, emission light L2 from the sensing surface 1s is output to the outside of the sample cell 30 through the window 32 and detected. The emission light L2 includes two-photon excitation fluorescence or multi-photon excitation fluorescence of fluorescent marker Lu.

The power of a specular reflection component of the measurement light L1 at the light-transmissive window 32 is high. If the measurement light L1 is mixed with the emission light L2 and detected, the S/N ratio becomes lower. Therefore, in the sensor with the sample cell 2, it is desirable that an angle formed by the window 32 and the sensing surface 1s can be adjusted so that the specular reflection component and the emission light L2 are separately detected.

"Sensing Apparatus"

Figure 7:
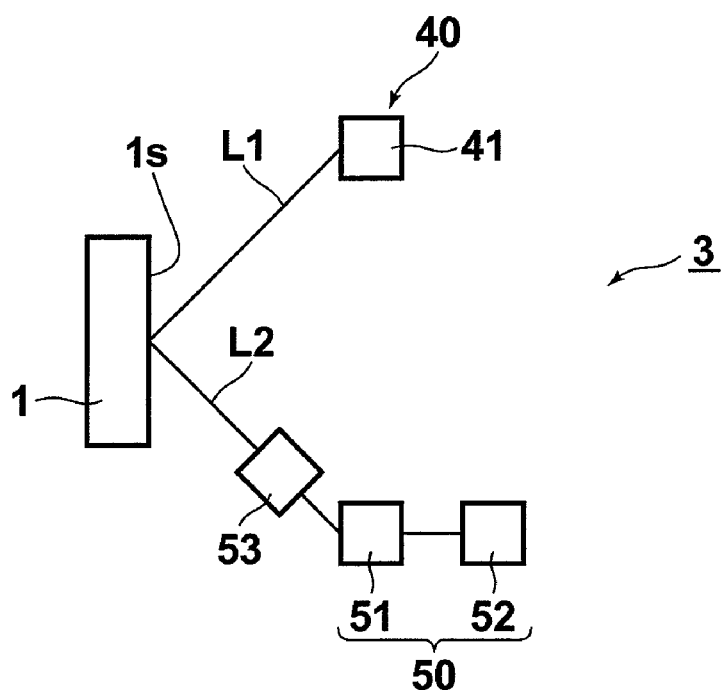
FIG. 7 is a diagram illustrating the structure of a sensing apparatus according to an embodiment of the present invention.

The structure of a sensing apparatus according an embodiment of the present invention will be described with reference to FIG. 7. As illustrated in FIG. 7, a sensing apparatus 3 includes the sensor 1 according to the aforementioned embodiment, a light illumination means (light emission means) 40 for emitting measurement light L1 to the sensor 1 and a detection means 50. The detection means 50 detects one of two-photon excitation fluorescence and multi-photon excitation fluorescence of fluorescent marker Lu. The two-photon excitation fluorescence or multi-photon excitation fluorescence is included in emission light L2 emitted from the sensor 1.

In the sensor 1, the sensing surface 1s is illuminated with measurement light L1. The measurement light L1 has a wavelength that can excite localized plasmons at the metal portion 20 and an absorption wavelength of the fluorescent marker Lu, at which the fluorescent marker emits one of two-photon excitation fluorescence and multi-photon excitation fluorescence. Therefore, the light illumination means 40 includes a single-wavelength light source 41, such as a laser and a light emission diode, that can emit light, the wavelength of which can excite localized plasmons in the metal portion 20, and which is an absorption wavelength of the fluorescent marker Lu, at which the fluorescent marker Lu emits one of the two-photon excitation fluorescence and the multi-photon excitation fluorescence. The light illumination means 40 includes a light-guide optical system that includes a collimator lens for collimating light emitted from the single-wavelength light source 41 and/or a condensing lens or the like, if necessary.

The detection means 50 includes a light intensity detector 51, such as a photodiode, and a data processing unit 52. The light intensity detector 51 detects one of two-photon excitation fluorescence and multi-photon excitation fluorescence in the emission light L2. It is desirable that light, such as a specular reflection component of the measurement light L1, that has the same wavelength as the measurement light L1 is not detected so that emitted fluorescence is detected at a higher sensitivity. The specular reflection component of the measurement light L1 acts as intense background light. For the purpose of preventing detection of light that has the same wavelength as that of the measurement light L1, a detector that does not detect light that has the same wavelength as that of the measurement light L1 is used as the light intensity detector 51. Alternatively, a wavelength selection means 53 may be provided in a light path between the detection means 50 and the sensor 1. The wavelength selection means 53 removes light that has the same wavelength as that of the measurement light L1.

The sensing apparatus 3 performs sensing using the sensor 1 according to the aforementioned embodiment. Therefore, the substance R to be detected is marked with fluorescent marker Lu that selectively binds to the substance R to be detected. In the sensing apparatus 3, it is possible to emit two-photon excitation fluorescence or multi-photon excitation fluorescence of the fluorescent marker Lu at high fluorescence efficiency. Further, it is possible to detect fluorescence emitted from the fluorescent marker Lu at a high S/N ratio. Further, as illustrated in FIG. 7, the sensing apparatus 3 does not require a complicated optical system in the measurement system. Therefore, the structure of the sensing apparatus 3 is simple. In the sensing apparatus 3, presence of the substance R to be detected and/or the amount of the substance R to be detected can be analyzed.

The sensor of the present invention is appropriate for use in fluorescence analysis that is performed in immunity measurement in the field of biochemistry.

What is claimed is:

1. A sensor used in sensing, the sensor comprising:
   a sensing surface, to which a specific substance to be detected can bind, wherein sensing is performed by marking the substance to be detected with a fluorescent marker that selectively binds to the substance to be detected and by detecting one of two-photon excitation fluorescence and multi-photon excitation fluorescence of the fluorescent marker, the sensor further comprising:
   a metal portion, at least a portion of which is exposed at the sensing surface, and in which localized plasmons can be excited, wherein the sensing surface is illuminated with measurement light having a wavelength that can excite localized plasmons in the metal portion and that is an absorption wavelength of the fluorescent marker, at which the fluorescent marker emits one of the two-photon excitation fluorescence and the multi-photon excitation fluorescence; and
   wherein a substrate of the metal portion is made of a dielectric that has a plurality of minute pores formed therein, and wherein the plurality of minute pores have openings at least at the sensing-surface-side surface of the dielectric, and wherein the metal portion is formed by a plurality of metal elements, each including a filled portion formed by filling a minute pore in the dielectric and a projection portion formed on the filled portion in such a manner that the projection portion projects from the surface of the dielectric, and wherein the diameter of the projection portion is greater than that of the filled portion.

2. A sensor, as defined in claim 1, wherein the metal portion has uneven structure, the size of which is less than the wavelength of the measurement light.

3. A sensor, as defined in claim 1, wherein the dielectric is formed by a metal oxide body that is obtained by anodizing at least a part of a metal body to be anodized, and wherein the plurality of minute pores are formed in the metal oxide body in the process of anodization.

4. A sensor, as defined in claim 1, wherein the localized plasmon resonance wavelength of the metal portion is substantially the same as the absorption wavelength of the fluorescent marker, at which the fluorescent marker emits one of the two-photon excitation fluorescence and the multi-photon excitation fluorescence, and wherein light that has the wavelength is used as the measurement light.

5. A sensor, as defined in claim 1, wherein a transparent insulation layer is formed on the surface of the metal portion.

6. A sensor, as defined in claim 1, wherein surface modification that selectively binds to the substance to be detected is provided on the surface of the metal portion.

7. A sensor, as defined in claim 1, wherein the sensing surface has been divided into a plurality of sensing areas, in each of which sensing is performed independently.

8. A sensor, as defined in claim 7, wherein surface modification that selectively binds to the substance to be detected is provided on the surface of the metal portion, and wherein the sensing surface includes the plurality of sensing areas, in each of which sensing is performed independently, and wherein a different kind of surface modification that is targeted at a different kind of substance to be detected is provided on each of the plurality of sensing areas.

9. A sensor, as defined in claim 1, wherein the sensor is attached to a sample cell in such a manner that the metal portion contacts with a sample in the sample cell, and wherein at least a portion of the sample cell, the portion through which the measurement light and light emitted from the sensing surface pass, transmits light, and wherein the light emitted from the sensing surface includes one of the two-photon excitation fluorescence and the multi-photon excitation fluorescence of the fluorescent marker.

10. A sensing apparatus comprising:
   a sensor, as defined in claim 1;
   a light illumination means for illuminating the sensor with the measurement light; and
   a detection means for detecting one of the two-photon excitation fluorescence and the multi-photon excitation fluorescence of the fluorescent marker, the one of which is included in light emitted from the sensor.

11. A sensing apparatus, as defined in claim 10, further comprising:
   a wavelength selection means for removing light that has the same wavelength as that of the measurement light, and wherein the wavelength selection means is provided in a light path between the sensor and the detection means.

12. A sensing apparatus, as defined in claim 10, wherein presence of the substance to be detected and/or the amount of the substance to be detected is analyzed.

13. A sensing method comprising the steps of:
   marking a substance to be detected with a fluorescent marker that selectively binds to the substance to be detected; and
   detecting one of two-photon excitation fluorescence and multi-photon excitation fluorescence of the fluorescent marker, wherein the one of two-photon excitation fluorescence and multi-photon excitation fluorescence is detected by generating the one of two-photon excitation fluorescence and multi-photon excitation fluorescence by exciting the fluorescent marker by a localized plasmon electric field at a sensing surface where the substance and the fluorescent marker are deposited,
   wherein the sensing surface includes a metal portion made of a dielectric that has a plurality of minute pores formed therein, and wherein the plurality of minute pores have openings at least at the sensing-surface-side surface of the dielectric, and wherein the metal portion is formed by a plurality of metal elements, each including a filled portion formed by filling a minute pore in the dielectric and a projection portion formed on the filled portion in such a manner that the projection portion projects from the surface of the dielectric, and wherein the diameter of the projection portion is greater than that of the filled portion.

* * * * *